United States Patent
Shirley et al.

(10) Patent No.: US 9,173,703 B1
(45) Date of Patent: Nov. 3, 2015

(54) NON-LINEAR ELECTROSURGICAL ELECTRODE EXTENDER

(75) Inventors: Ben D. Shirley, Salt Lake City, UT (US); Mark L. Fox, Salt Lake City, UT (US)

(73) Assignee: UTAH MEDICAL PRODUCTS INC., Salt Lake City, UT (US)

( * ) Notice: Subject to any disclaimer, the term of this patent is extended or adjusted under 35 U.S.C. 154(b) by 1221 days.

(21) Appl. No.: 12/962,379

(22) Filed: Dec. 7, 2010

(51) Int. Cl.
*A61B 18/14* (2006.01)
*A61B 18/00* (2006.01)

(52) U.S. Cl.
CPC ... *A61B 18/1485* (2013.01); *A61B 2018/00559* (2013.01); *A61B 2018/1407* (2013.01); *A61B 2018/1495* (2013.01)

(58) Field of Classification Search
CPC ............. A61B 18/082; A61B 18/1482; A61B 18/1485; A61B 2018/00559; A61B 2018/1495; A61B 2018/1407; A61B 2560/0431
USPC ................................. 606/41, 46; 607/99, 138
See application file for complete search history.

(56) References Cited

U.S. PATENT DOCUMENTS

| 5,957,923 A * | 9/1999 | Hahnen ............... A61B 18/1485 606/46 |
| 8,425,509 B2 * | 4/2013 | Longo ............. A61B 17/320016 606/45 |
| 2001/0025177 A1 * | 9/2001 | Woloszko ............... A61B 18/12 606/41 |

* cited by examiner

*Primary Examiner* — Michael Peffley
*Assistant Examiner* — Thomas Giuliani
(74) *Attorney, Agent, or Firm* — Kirton McConkie; Evan R. Witt

(57) ABSTRACT

A non-linear electrosurgical electrode extender is disclosed. The extender includes a shaft at a proximal end thereof, a receiver at a distal end thereof, and a curved body portion extending between the shaft and the receiver. The shaft fits in an electrosurgical handpiece that defines a handpiece central axis. The receiver receives the electrosurgical electrode. The curved body portion is disposed outside the handpiece central axis and positions the receiver at a converging angle relative to the handpiece central axis such that when the electrosurgical electrode is disposed in the receiver, a surgically active distal end of the electrode intersects the handpiece central axis. The electrode extender is adapted for use with wire loop gynecologic electrosurgical electrode in gynecologic procedures. The extender maintains the tactility and control of a straight electrode extender while permitting the handpiece to be disposed outside the cervix view axis.

19 Claims, 2 Drawing Sheets

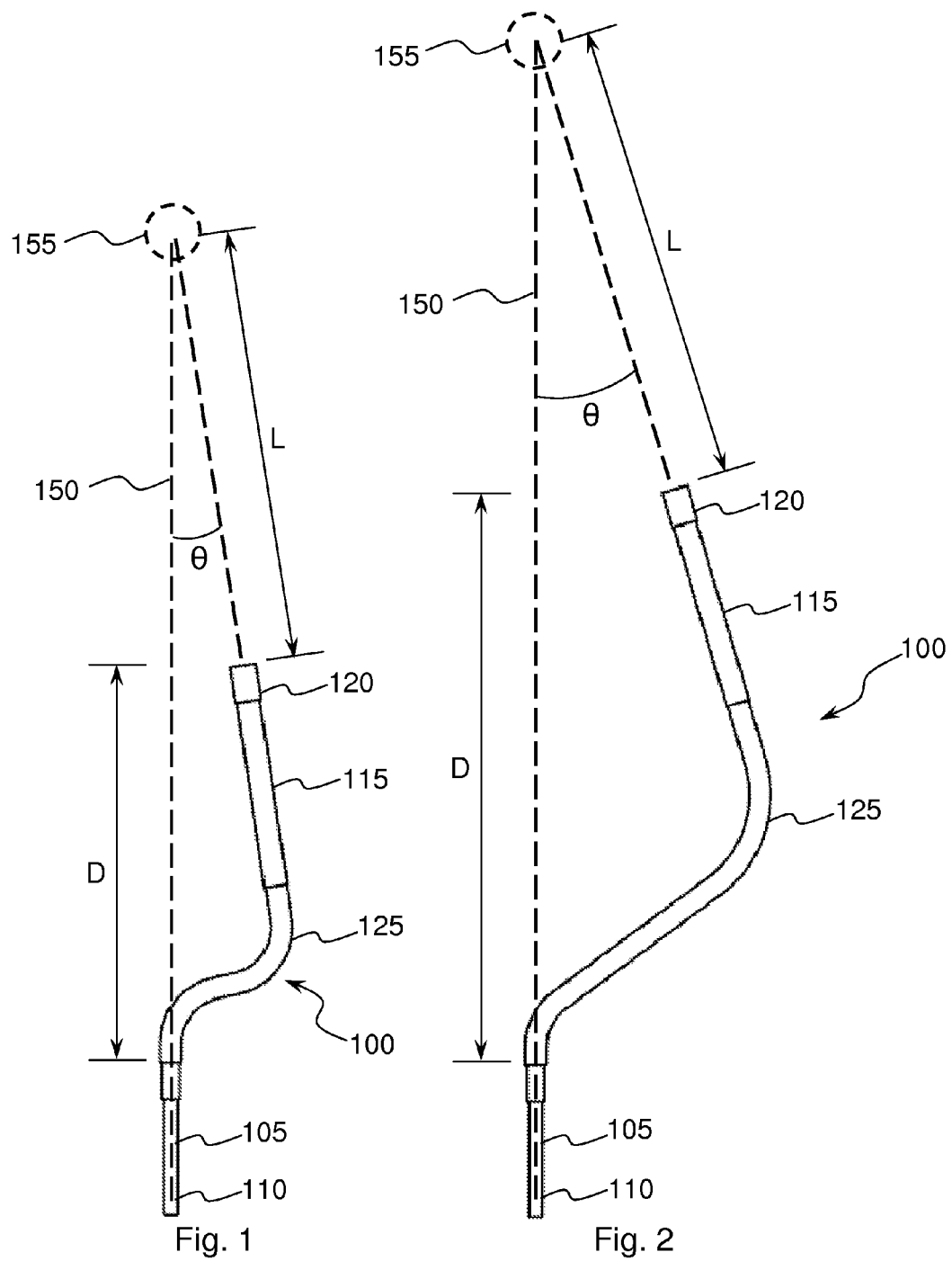

NON-LINEAR ELECTROSURGICAL ELECTRODE EXTENDER

BACKGROUND OF THE INVENTION

This disclosure relates to a non-linear electrosurgical electrode extender. More specifically, the disclosure relates to an electrode extender which is curved to orient an electrosurgical electrode coupled to the extender in a manner that the surgically active end of the electrode falls within a handpiece central axis, as if the electrode extender were linear. The curved electrode extender positions the electrode handpiece away from a colposcope to avoid interference with a colposcope body in gynecologic procedures where a colposcope is used.

Electrosurgical electrodes are used in many different surgical procedures. The electrodes may have a specialized shape and configuration adapted for a particular surgical procedure, such as certain gynecologic procedures. One such procedure is Loop Excision of the Transformation Zone (LETZ). Medical literature also refers to the LETZ procedure as the Loop Electrosurgical Excision Procedure (LEEP). The LETZ procedure uses a thin wire loop electrode to remove cervical lesions. The wire loop may have various sizes and shapes. One commercially available electrode is the UtahLoop® round loop electrode available from Utah Medical Products, Inc., Midvale, Utah. The wire loop electrode is attached to a handpiece (sometimes referred to as an electrosurgical pencil, pen, or chuck), which is a hand-held device that holds the electrode. The handpiece is coupled to an electrosurgical generator which generates an electric current that heats and cuts cervical tissue cells close to the wire loop. A colposcope is often used to allow the gynecologist to clearly see the cervix during the electrosurgical procedure.

Cervical depth varies among patients. Gynecologic electrosurgical electrode lengths that are appropriate for one patient may be insufficient to reach another patient's cervix. A traditional straight electrode extender can provide adequate reach, but the additional length may cause handpiece interference with the colposcope body or block the cervical view. In some cases, the handpiece, without an extender, can be obstructed by the colposcope body. In other cases visual obstruction of the cervix can occur during direct visualization when a colposcope is not used. Moreover, sometimes other equipment and instruments, or even the clinician's hand, may block the cervical view.

Accordingly, it would be an improvement in the art to provide an electrosurgical electrode extender that avoids handpiece interference with the colposcope body. It would be a further advancement in the art to provide an electrosurgical electrode extender that does not block the cervical view axis.

BRIEF SUMMARY OF THE INVENTION

This disclosure discusses an electrosurgical electrode extender. The electrosurgical electrode extender includes a shaft at a proximal end thereof, a receiver at a distal end thereof, and a curved body portion that joins the receiver to the metal shaft.

The shaft is sized and configured to be inserted and held within an electrosurgical handpiece. The shaft includes an electrically conductive element to permit electrical connection with the handpiece. In one embodiment, the shaft is a metal shaft. In another embodiment the shaft comprises a metal core surrounded by a non-metallic material. The handpiece is held by the gynecologist or surgeon performing the electrosurgical procedure. The handpiece is designed to hold the electrosurgical electrode. The extender is inserted and held within the electrosurgical handpiece in the same manner as the electrosurgical electrode. The handpiece defines a handpiece central axis. The shaft is linear and when inserted and held within the handpiece, the shaft is collinear with the handpiece central axis. The handpiece is electrically coupled to an electrosurgical generator which generates an electric current that heats the surgically active distal end of the electrosurgical electrode and cuts tissue cells. In one embodiment, the shaft is electrically uninsulated and the curved body portion is electrically insulated.

The receiver is sized and configured to receive the electrosurgical electrode in the same manner as the handpiece receives the electrode.

The curved body portion extends between the shaft and the receiver. The body portion is disposed outside the handpiece central axis. The curved body portion positions and orients the receiver at a converging angle relative to the handpiece central axis such that when the electrosurgical electrode is disposed in the receiver, the surgically active end of the electrode intersects the handpiece central axis. In one embodiment, the body portion is S shaped.

In one embodiment, the electrosurgical electrode is a wire loop electrode configured for a gynecological procedure.

The electrode extender extends the surgically active distal end of the electrode along the handpiece central axis. In one embodiment, the surgically active distal end is extended along the handpiece central axis a distance in the range from about 5 cm to 10 cm. In another embodiment, the electrode extender extends the surgically active distal end of the electrode along the handpiece central axis a distance of about 6 cm±1 cm. In another embodiment, the electrode extender extends the surgically active distal end of the electrode along the handpiece central axis a distance of about 9 cm±1 cm.

The larger size electrode extender may be useful during colposcopically visualized LETZ procedures. It provides adequate clearance of the electrosurgery handpiece from the body of the colposcope. The small size electrode extender may be useful during directly visualized LETZ procedures. It keeps the user's hand away from the visual axis.

These features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates a non-linear electrosurgical electrode extender according to a first embodiment within the scope of the present invention.

FIG. 2 illustrates a non-linear electrosurgical electrode extender according to a second embodiment within the scope of the present invention.

DETAILED DESCRIPTION OF THE INVENTION

Figure 3:
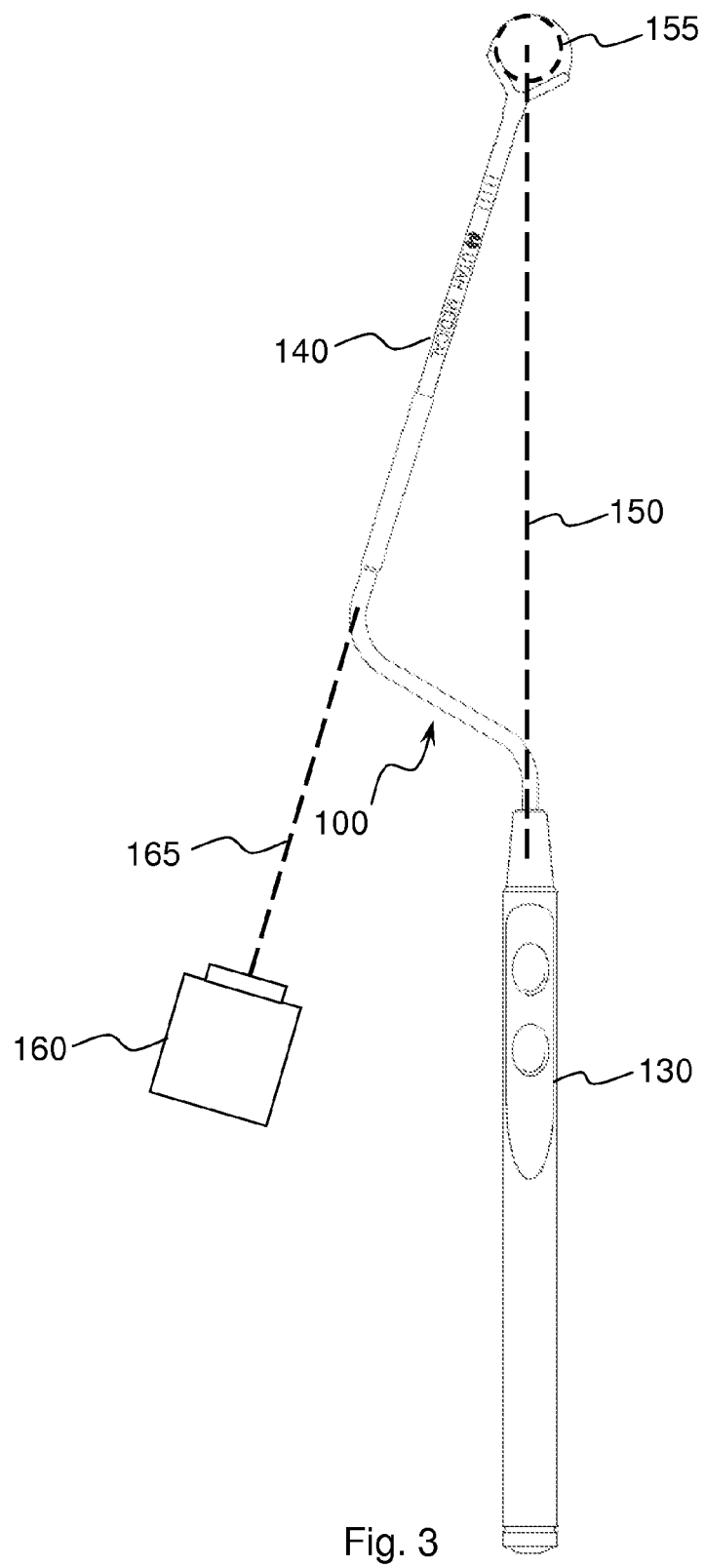
FIG. 3 illustrates a non-linear electrosurgical electrode extender as it may be used with an electrosurgical handpiece, an electrosurgical electrode, and a colposcope.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are offered to provide a thorough understanding of embodiments of the invention. One skilled in the relevant art will recognize, however, that the invention may be practiced without one or more of the specific details or methods, or with other methods, components, characteristics, materials, and so forth. In other instances, well-known structures, materials, or operations are not shown or described in detail to avoid obscuring aspects of the invention.

The embodiments of the present invention will be best understood by reference to the drawings, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the electrode extender as represented in FIGS. 1 through 3, is not intended to limit the scope of the invention, as claimed, but is merely representative of the embodiments of the invention.

The present invention is drawn to an electrode extender. FIGS. 1 and 2 illustrate two different sized electrosurgical electrode extenders 100 within the scope of the present invention. The electrosurgical electrode extender 100 includes a shaft 105 at a proximal end 110 thereof, a receiver 115 at a distal end 120 thereof, and a curved body portion 125 that joins the receiver 115 to the shaft 105.

The shaft 105 has a similar size and configuration to a corresponding shaft of the electrosurgical electrode. The shaft 105 is sized and configured to be inserted and held within an electrosurgical handpiece 130, as shown in FIG. 3, in the same way that the handpiece 130 is designed to hold the electrosurgical electrode 140. The handpiece 130, sometimes referred to as an electrosurgical pencil, pen, or chuck, is held by the gynecologist or surgeon performing the electrosurgical procedure. The shaft 105 of the extender 100 is inserted and held within the electrosurgical handpiece 130 in the same manner as the electrosurgical electrode 140 is inserted and held with the electrosurgical handpiece 130, without an extender. The handpiece 130 defines a handpiece central axis 150 which extends in the general longitudinal direction of the handpiece. The shaft 105 is linear and when inserted and held within the handpiece 130, the shaft is collinear with the handpiece central axis 150. In use, the handpiece 130 is electrically coupled to an electrosurgical generator (not shown) which generates an electric current that heats and cuts tissue cells at a surgically active distal end 155 of the electrosurgical electrode 140. One non-limiting example of an electrosurgical generator is the FINESSE® Electrosurgical generator system provided by Utah Medical Products, Inc., Midvale, Utah. In one embodiment, the shaft 105 provides electrical connection with the handpiece.

The receiver 115 is sized and configured to receive the electrosurgical electrode 140 in the same manner as the handpiece 130 receives the electrode 140. The receiver provides secure electrical coupling with the electrosurgical electrode.

The curved body portion 125 extends between the shaft 105 and the receiver 115. The body portion 125 is disposed outside the handpiece central axis 150. The curved body portion 125 positions and orients the receiver 115 at a converging angle θ relative to the handpiece central axis 150 such that when the electrosurgical electrode 140, having a length L is disposed in the receiver 115, the surgically active end 155 of the electrode 140 intersects the handpiece central axis 150. In one embodiment, the body portion 125 is S shaped. In one embodiment, the curved body portion 125 is electrically insulated to protect the user, the patient, and others who may contact the curved body portion.

In one embodiment, the electrosurgical electrode 140 is a wire loop electrode configured for a gynecological procedure, such as the LETZ procedure.

The electrode extender 100 extends the surgically active distal end 155 of the electrode 140 along the handpiece central axis. In one embodiment, the surgically active distal end is extended along the handpiece central axis 150 a distance D. In one embodiment, the distance D may range from about 5 cm to 10 cm. In another embodiment, the electrode extender extends the surgically active distal end of the electrode along the handpiece central axis a distance of about 6 cm±1 cm. In another embodiment, the electrode extender extends the surgically active distal end of the electrode along the handpiece central axis a distance of about 9 cm±1 cm.

The larger size electrode extender 100 may be useful during colposcopically visualized LETZ procedures. It provides adequate clearance of the electrosurgery handpiece 130 from the body of the colposcope 160. The small size electrode extender may be useful during directly visualized LETZ procedures. It keeps the clinician's hand and handpiece away from the visual axis.

The disclosed electrosurgical extender is particularly useful for gynecologic electrodes designed for the LETZ procedures to create additional reach for patients with a deeper cervix. The electrode extender is curved to reposition the gynecologist's hand and electrode handpiece away from the colposcope body 160 and cervix view axis 165, as shown in FIG. 3. The curved electrode extender orients the electrosurgical electrode in a manner that the surgically active end 155 of the electrode, such as a wire loop, falls within the handpiece central axis 150 of the device, as if the electrode extender were linear.

Electrosurgical electrode tactility is important during LETZ excisions. Because the surgically active end 155 is oriented along the handpiece central axis 150, the curved electrode extender 100 maintains the tactility and control of a straight electrode extender while permitting the gynecologist's hand and handpiece to be disposed outside the cervix view axis 165. This eliminates lateral force on the electrode which would cause torque and result in slippage of the extender in the handpiece.

While specific embodiments of the present invention have been illustrated and described, numerous modifications come to mind without significantly departing from the spirit of the invention, and the scope of protection is only limited by the scope of the accompanying claims.

The invention claimed is:

1. A non-linear electrosurgical electrode extender for use with an electrosurgical electrode having a shaft portion and an electrode portion at a surgically active distal end of the electrode, said electrode extender comprising: a shaft at a proximal end thereof, a proximal end of the shaft being sized and configured to be coupled to an electrosurgical handpiece, the proximal end of the shaft extending along a first axis; a receiver at a distal end thereof, a distal end of the receiver being sized and configured to removably receive the shaft portion of the electrosurgical electrode; and a curved body portion extending between a distal end of the shaft and a proximal end of the receiver, and forming a first bend in a first plane and a second bend in the first plane, the first bend causing the body portion to extend within the first plane along a second axis, the second bend causing the receiver to extend within the first plane along a third axis, a direction of the first bend being opposite a direction of the second bend, an angle of the second bend with respect to the second axis being greater than an angle of the first bend with respect to the first axis such that the third axis intersects the first axis at a point distal to the second bend, a length of the receiver being configured such that the receiver does not intersect the first axis.

2. The electrosurgical electrode extender as defined in claim 1, wherein the proximal end of the shaft is configured to be removably inserted into the electrosurgical handpiece along a central axis of the electrosurgical handpiece.

3. The electrosurgical electrode extender as defined in claim 2, wherein when the proximal end of the electrode extender shaft is coupled to the electrosurgical handpiece, the first axis and the central axis of the electrosurgical handpiece are collinear.

4. The electrosurgical electrode extender as defined in claim 2, wherein the electrode extender extends the surgically active distal end of the electrode along the central axis of the electrosurgical handpiece a distance in the range from about 5 cm to 10 cm.

5. The electrosurgical electrode extender as defined in claim 2, wherein the electrode extender extends the surgically active distal end of the electrode along the central axis of the electrosurgical handpiece a distance of about 6 cm±1 cm.

6. The electrosurgical electrode extender as defined in claim 2, wherein the electrode extender extends the surgically active distal end of the electrode along the central axis of the electrosurgical handpiece a distance of about 9 cm±1 cm.

7. The electrosurgical electrode extender as defined in claim 1, wherein the shaft is electrically uninsulated and the curved body portion is electrically insulated.

8. A non-linear electrosurgical electrode extender for use with an electrosurgical electrode having a shaft portion and an electrode portion at a surgically active distal end of the electrode, said electrode extender comprising: a metal shaft at a proximal end thereof, a proximal end of the metal shaft being sized and configured to be removably inserted and held within an electrosurgical handpiece electrically connected to an electrosurgical generator that provides electric power to the electrosurgical electrode, wherein the handpiece defines a first axis, wherein the proximal end of the metal shaft is linear and when inserted and held within the handpiece, the proximal end of the metal shaft is collinear with the first axis; a receiver at a distal end thereof, a distal end of the receiver being sized and configured to removably receive the shaft portion of the electrosurgical electrode; and a curved body portion extending between a distal end of the shaft and a proximal end of the receiver, and forming a first bend in a first plane and a second bend in the first plane, the first bend causing the body portion to extend within the first plane along a second axis, the second bend causing the receiver to extend within the first plane along a third axis, a direction of the first bend being opposite a direction of the second bend, an angle of the second bend with respect to the second axis being greater than an angle of the first bend with respect to the first axis such that the third axis intersects the first axis at a point distal to the second bend, a length of the receiver being configured such that the receiver does not intersect the first axis.

9. The electrosurgical electrode extender as defined in claim 8, wherein the metal shaft is electrically uninsulated and the body portion is electrically insulated.

10. The electrosurgical electrode extender as defined in claim 8, wherein the proximal end of the metal shaft is configured to be removably inserted into the electrosurgical handpiece along the first axis of the electrosurgical handpiece.

11. The electrosurgical electrode extender as defined in claim 10, wherein the electrode extender extends the surgically active distal end of the electrode along the first axis of the electrosurgical handpiece a distance of about 6 cm±1 cm.

12. The electrosurgical electrode extender as defined in claim 10, wherein the electrode extender extends the surgically active distal end of the electrode along the first axis of the electrosurgical handpiece a distance of about 9 cm±1 cm.

13. An electrosurgical assembly comprising: an electrosurgical electrode having a shaft portion and an electrode portion at a surgically active distal end of the electrode, the electrode portion being secured within the shaft portion; and an electrosurgical electrode extender comprising: a shaft at a proximal end thereof, a proximal end of the shaft being sized and configured to be removably coupled to an electrosurgical handpiece, the proximal end of the shaft extending along a first axis; a receiver at a distal end thereof, a distal end of the receiver being sized and configured to removably receive the shaft portion of the electrosurgical electrode; and a curved body portion extending between a distal end of the shaft and a proximal end of the receiver, and forming a first bend in a first plane a the second bend in the first plane, the first bend causing the body portion to extend within the first plane along a second axis, the second bend causing the receiver to extend within the first plane along a third axis, a direction of the first bend being opposite a direction of the second bend, an angle of the second bend with respect to the second axis being greater than an angle of the first bend with respect to the first axis such that the third axis intersects the first axis at a point distal to the second bend, a length of the receiver being configured such that the receiver does not intersect the first axis.

14. The electrosurgical assembly of claim 13, wherein the length of the receiver portion and a length of the electrosurgical electrode are configured to cause the electrode portion of the electrosurgical electrode to be positioned at the first axis.

15. The electrosurgical assembly of claim 13, wherein the electrosurgical handpiece has a central axis and when the proximal end of the electrode extender shaft is coupled to the electrosurgical handpiece, the first axis and the handpiece central axis are collinear.

16. The electrosurgical assembly of claim 15, wherein the electrode extender extends the surgically active distal end of the electrode along the central axis of the electrosurgical handpiece a distance of about 6 cm±1 cm.

17. The electrosurgical assembly of claim 15, wherein the electrode extender extends the surgically active distal end of the electrode along the central axis of the electrosurgical handpiece a distance of about 9 cm±1 cm.

18. The electrosurgical assembly of claim 13, wherein the electrode portion of the electrosurgical electrode comprises a wire loop that is secured within the shaft portion.

19. The electrosurgical assembly of claim 18, wherein the shaft portion of the electrosurgical electrode has a similar size and configuration as the shaft of the electrosurgical electrode extender.

\* \* \* \* \*